(12) United States Patent
Cummins

(10) Patent No.: US 6,242,011 B1
(45) Date of Patent: *Jun. 5, 2001

(54) ACIDIC COMPOSITION OF MATTER FOR USE TO DESTROY MICROORGANISMS

(76) Inventor: Barry W. Cummins, 1203 Egret Ave., Fort Pierce, FL (US) 34982

( * ) Notice: Subject to any disclaimer, the term of this patent is extended or adjusted under 35 U.S.C. 154(b) by 0 days.

This patent is subject to a terminal disclaimer.

(21) Appl. No.: 09/369,096

(22) Filed: Aug. 5, 1999

(51) Int. Cl.[7] .......................... A01N 59/02; A01N 47/28; A61K 33/04; A61K 31/17; A61L 2/18
(52) U.S. Cl. .......................... 424/710; 424/703; 424/709; 424/713; 514/588; 514/886; 514/887; 422/12; 422/28; 422/29; 422/905; 426/532; 252/183.11; 252/183.12; 252/183.13; 252/183.14; 504/151
(58) Field of Search .................................. 424/703, 710, 424/713, 709; 514/588, 886, 887; 422/12, 28, 29, 905; 426/532; 252/183.11, 183.12, 183.13, 183.14; 504/151

(56) References Cited

U.S. PATENT DOCUMENTS

| | | | | |
|---|---|---|---|---|
| 3,919,416 | * | 11/1975 | Cosby | 424/710 |
| 3,923,983 | * | 12/1975 | Pensack | 424/709 |
| 4,116,664 | * | 9/1978 | Jones | 71/29 |
| 4,310,343 | * | 1/1982 | Verdegaal et al. | 71/28 |
| 4,402,852 | * | 9/1983 | Young | 71/28 |
| 4,404,116 | * | 9/1983 | Young | 71/28 |
| 4,445,925 | * | 5/1984 | Young | 71/28 |
| 4,564,504 | * | 1/1986 | Sorber | 422/189 |
| 4,673,522 | * | 6/1987 | Young | 134/19 |
| 4,776,963 | * | 10/1988 | Inagaki et al. | 210/764 |
| 4,817,333 | * | 4/1989 | Szepessy et al. | 47/58.1 |
| 5,185,151 | * | 2/1993 | Young | 424/400 |
| 5,989,595 | * | 11/1999 | Cummins | 424/710 |

OTHER PUBLICATIONS

Medline Abstract, Accession No. 75126719, 1975.*

* cited by examiner

*Primary Examiner*—John Pak
(74) *Attorney, Agent, or Firm*—Malin, Haley & Dimaggio, P.A.

(57) ABSTRACT

A composition of matter and the method of making that provides a low pH acidic composition that is useful for destroying microorganisms that are undesirable and useful for destroying or reducing melanoma on human skin. The composition and method include sulfuric acid combined with distilled water and ammonium sulfate under at least 15 psi pressure in a pressurized container, all of which is heated to approximately 800° F. or more for at least 3 hours. The final cooled mixture is stabilized with 10 percent of the original mixture. The resultant composition is useful for preserving food, such as fresh fish, and for skin treatment of melanoma.

5 Claims, No Drawings

ACIDIC COMPOSITION OF MATTER FOR USE TO DESTROY MICROORGANISMS

BACKGROUND OF THE INVENTION

1. Field of the Invention

This invention relates to a composition of matter and the method of making improved acidic compositions that are useful for the treatment of killing bacteria or other potentially toxic cells, including disease cells, and specifically to an improved composition of matter and the method of making that can be used as a bactericide, fungicide, viricides, and for the treatment of skin diseases.

2. Description of the Prior Art

The use of acids and acidic chemicals for killing deleterious organic organisms, such as bacteria, germs, and viruses is well known in the art. Chlorine or hydrochloric acid is especially useful as a bactericide and is used universally as a cleaning agent.

Bacteria plays an important role in the deterioration of human foodstuffs. Foods such as fish are particularly susceptible to rapid deterioration, especially at room temperature, and compounds for the preservation of foods or the retardation of bacteria growth have been employed in the past. One of the problems with such compounds is that in certain increased levels, they can be toxic to human beings, thereby defeating the purpose of preserving the foodstuffs.

Because of the extremely acidic nature of some of the bactericides and viricides that have been utilized in the past, oftentimes they can cause skin irritation or other side effects for human beings coming in contact with these compositions, or can even be fatal if accidentally consumed. Chlorine has had other negative implications in terms of the environment, and has not been environmentally friendly because of the release of chlorine gas into the environment.

The present invention provides for a composition of matter and the method of making it that produces a composition that operates in a very low pH range to provide toxicity to bacteria, virus, and certain malignant cells that attack human skin determatologically, while at the same time proving to be non-toxic to human beings and not harmful to healthy human cells.

The use of the invention has been found to be helpful as a bactericide for preserving fresh food items, such as fish, for long periods of time without toxically endangering the food product, and has also been found useful as a dermatological composition to reduce or eliminate melanoma of the skin as a skin care product.

SUMMARY OF THE INVENTION

A composition of matter formed by the following described method has been found to be an effective bactericide, fungicide, viricide, and low pH acid that is non-toxic to healthy human cells.

The first basic ingredient used is sulfuric acid, preferably of around 98 percent purity. The sulfuric acid is placed in a container at a predetermined quantity. The next step is to place distilled water in a separate container and heat said water to 140° F., at which time 2.77 lbs. per gallon of 21 percent active ammonium sulfate is added to the water using a 316L stainless tube to inject air to dissolve the ammonium sulfate in the $H_2O$.

The mixture of sulfuric acid, distilled water, and ammonium sulfate are themselves injected simultaneously at the predetermined ratio into a pressure vessel, preferably made of stainless steel, the volume of which is significantly larger than the total amount of composition to be obtained. The overall mixture is sprayed by nozzles into the pressure vessel, which is maintained at 15 psi above atmospheric pressure. At approximately the 1 ft. of liquid level, a plurality of electrodes are disposed to contact the liquid as it fills the pressure vessel, with a predetermined amount of DC current (amperage) provided. The positive and negative electrodes are spaced approximately 3 ft. apart. A DC voltage and current of at least one amp is provided. High pressure air is also forced into the liquid from radially disposed radial pipes to cause the overall mixture to rotate vigorously within the pressure vessel.

The pressure vessel will also include a cooling jacket. The temperature of the mixture is heated not to exceed 1200° F. and kept at this temperature for 3 to 4 hours. The pressure vessel permits for release of gas, which is believed to be hydrogen gas, coming off the mixture.

The mixture is then cooled down to room temperature, at which time a stabilizer, which is 10 percent of the total weight of the original mixture, is introduced into the cool-down mixture. The overall composition of the matter is then ready for use, either as a fresh food preservative, or can be implemented with various skin creams that are carriers for use in dermatology for reducing or eliminating melanoma on human skin.

For use as a food preservative, the composition of the matter is coated over items such as fresh fish, with the composition acting as a bacteria retardant.

The pressure vessel may be made of stainless steel, as are the electrodes used therein.

In an alternate embodiment, the ammonium sulfate mixture may be replaced by a 46 percent urea substitute, with the methodology being the same as for the ammonium sulfate composition.

The composition arrived at may be diluted down further, depending on the particular use, with additional distilled water, much like a typical acid. Applicant has found that although the pH is low (below 2), the composition is not deleterious or toxic to health human cells, and does not cause irritation to humans when coming in contact with the material.

It is an object of this invention to provide an improved composition of matter that has desirable acidic (low pH) characteristics that are not harmful or deleterious to organic human cells to destroy microorganisms or in the treatment of skin diseases.

It is another object of this invention to provide an improved composition of matter and the method of making it to create a widely usable composition for bactericide, fungicide, and complete elimination and destruction of microorganisms that are toxic to human health.

But yet still another object of this invention is to create a composition of matter that has numerous applications in areas of bactericide, viricide, food preservation, and dermatological treatment of human skin cells to eliminate or reduce diseases of the skin.

In accordance with these and other objects which will become apparent hereinafter, the instant invention will now be described with particular reference to the accompanying drawings.

DESCRIPTION OF THE PREFERRED EMBODIMENT

The composition of matter forms a highly effective composition to kill or retard the growth of microorganisms, especially such as bacteria, viruses, and other microorganisms.

The first basic ingredient used is sulfuric acid, preferably of around 98 percent purity. The sulfuric acid is placed in a container at a predetermined quantity. The next step is to place distilled water in a separate container and heat said water to 140° F., at which time 2.77 lbs. per gallon of 21 percent active ammonium sulfate is added to the water using a 316L stainless tube to inject air to dissolve the ammonium sulfate in the $H_2O$.

The resultant ammonium sulfate, water, and sulfuric acid mixtures themselves are injected simultaneously at the same ratio into a large, stainless steel pressure vessel that is maintained at a pressure of at least 15 psi above atmospheric pressure. The mixture is forced into the pressure vessel, which itself has positive and negative electrodes for passing a DC current through the mixture as it is filled into the pressure vessel. At least one amp of DC current is maintained approximately 1 ft. above the base of the pressure vessel.

Sparges include spray head nozzle-like sprayers used to force the mixture in a sprayed-in form into the pressure vessel.

The temperature of the mixture is raised to approximately 1200° F., and is maintained for 3 to 4 hours. A cooling jacket is required to keep the temperature below 1200° F. During this process, excess gas is removed, which is believed to be hydrogen gas. A separate gas distributor is mounted within the liquid in the form of perpendicular sprayers that take air and inject it into the mixture during the heating process, which causes rotation of the fluid, creating a dynamic action in which the fluid is rotating about in the pressure vessel. After approximately 4 hours, the mixture is allowed to cool down to room temperature. At the end of the cool down period, another 10 percent of the total weight of the original mixture is added to the cooled down mixture to act as a stabilizer.

The resultant mixture has been found very suitable for direct use as a food preservative for preserving food such as fish for long periods of time, up to two weeks at room temperature, and when used dermatologically as a cream base has been found to reduce or eliminate skin cancers such as melanoma.

The exact chemical formula for the resultant composition is not clearly known.

Applicant has also found that urea can be added to form the mixture in place of the ammonium sulfate with equally effective results.

EXAMPLE 1

The first basic ingredient used is sulfuric acid, preferably of around 98 percent purity. The sulfuric acid is placed in a container at a predetermined quantity. The next step is to place distilled water in a separate container and heat said water to 140° F., at which time 2.77 lbs. per gallon of 21 percent active ammonium sulfate is added to the water using a 316L stainless tube to inject air to dissolve the ammonium sulfate in the $H_2O$.

Simultaneously, the $H_2SO_4$, and the $H_2O$, and the ammonium sulfate $(NH_4)_2SO_4$ are injected into a large 400 gallon, stainless steel vessel that is maintained at 15 psi above atmospheric pressure through a plurality of sprayers (sparges).

Air under pressure is also introduced through sprayers in the bottom of the container, perpendicular to the liquid mixture, which forces the liquid mixture to dynamically rotate within the pressure vessel.

Two electrodes, a cathode and anode, provide a DC voltage 1 ft. above the bottom of the contained at approximately 1 to 3 amps, with the electrodes being 3 ft. apart.

The mixture is heated to 1200° F. and maintained at that temperature for 3 to 4 hours, during which time excess hydrogen gas is removed.

After 4 hours, the mixture is allowed to return and cool down to room temperature. After cool down, an additional 10 percent of the same mixture is reintroduced into the original cool down mixture to act as a stabilizer. Other stabilizers can be substituted. The resultant composition can be used as is or diluted with distilled water as a fish preservative and as applied to the skin of the fish. This would be fish at room temperature that can be preserved for weeks without refrigeration.

The composition can also be added with effective dermatological creams, and without dilution to retard or destroy melanoma cancer cells on human skin.

EXAMPLE 2

The composition as shown in Example 1 can be altered by the substitution of urea for the ammonium sulfate in the amount of 46 percent active urea. The remainder of the methodology will be the same.

It is believed that numerous applications as a bactericide, a fungicide, a viricide or other active acidic cleaning agent can be used for the compound at extremely low pHs (below 2), while at the same time the composition is not an irritant or deleterious to healthy human cells.

The following is an alternate embodiment of the invention.

The mixture shall consist of sulfuric acid, water, and ammonium sulfate, or substitute 46 percent urea for the 21 per cent ammonium sulfate.

One pound of 21 percent ammonium sulfate for gallon of water up to five pounds of 21 percent ammonium sulfate per gallon of water (Distilled) with the ratio of water and ammonium sulfate to the sulfuric acid being from a 1 to 1 mixture up to a 5 to 1 mixture with the higher number being the water and ammonium sulfate mixture. Mixture ratios are by weight.

Temperature ranges are from 400° F. to 2400° F. and pressures range from 5 PSI to 800 PSI and DC voltage ranges are from 1 amp to 100 amps.

There are 4 things that effect the rate of reaction of the invention: temperature, pressure, amperage and amount of product being used. These four variables then determine how long the process takes.

EXAMPLE 3

Sulfuric acid, preferably around 98% purity, is placed in container in a predetermined quantity.

The next step is to place distilled water in a separate container and heat the water to approximately 140° F. at which time 2.77 pounds per gallon of 21 percent active ammonium sulfate is added to the water using a 316L stainless tube to inject air to dissolve the ammonium sulfate in the water.

Simultaneously, $H_2SO_4$ and $H_2O$ and the aluminum sulfate $(NH_4)_2SO_4$ are injected into the large 400 gallon stainless steel vessel that is maintained at 15 psi above atmospheric pressure through a plurality of sprayers (sponges).

Air under pressure is also introduced through sprayers in the bottom of the container, perpendicular to the liquid mixture, which forces the liquid mixture to dynamically rotate within the pressure vessel.

Two electrodes, a cathode and an anode provide a DC voltage one foot above the bottom of the container at approximately 3 amps with the electrodes being three feet apart.

The mixture is heated to 800° F. and maintained at that temperature for three to four hours during which time excess hydrogen gas is removed.

After four hours, the mixture is allowed to return and cool down to room temperature. After cool down, an additional lot of the same mixture is reintroduced into the original cool down mixture to act as a stabilizer. The result in composition can be used as is or diluted with distilled water as a fish preservative and as applied to the skin of the fish.

The instant invention has been shown and described herein in what is considered to be the most practical and preferred embodiment. It is recognized, however, that departures may be made therefrom within the scope of the invention and that obvious modifications will occur to a person skilled in the art.

What I claim is:

1. A composition of matter useful for the treatment of killing microorganism and human skin diseases, produced by the steps consisting of:
    combining sulfuric acid of 98% purity in a 1 to 2 volume ratio with distilled water and ammonium sulfate in a ratio of 2.77 lbs. of ammonium sulfate per gallon of distilled water to provide mixture (I);
    combining the mixture (I) in a pressurized vessel at a pressure that is 15 psi above atmospheric pressure and heating the mixture to at least 800 degrees Fahrenheit for at least 30 minutes;
    cooling the mixture; and
    after the mixture is cooled, adding a stabilizer which comprises 10 weight percent of the total weight of mixture (I).

2. The composition of claim 1, wherein once the mixture is heated, the mixture is stirred vigorously by air under pressure in said pressurized vessel.

3. The composition of claim 1, wherein the mixture is introduced under pressure into the pressurized vessel by spraying into the vessel.

4. A composition of matter useful for the treatment of killing microorganism and human skin diseases, produced by the steps consisting of:
    combining sulfuric acid of 98 percent purity in a 1 to 2 volume ratio with distilled water and urea in a ratio of 2.77 lbs. of urea per gallon of distilled water to provide mixture (II);
    combining the mixture (II) in a pressurized vessel at a pressure that is 15 psi above atmospheric pressure and heating the mixture to at least 800 degrees Fahrenheit for at least 3 hours;
    cooling the mixture; and
    after the mixture is cooled, adding a stabilizer which comprises 10 weight percent of the total weight of mixture (II).

5. A method of preparing a composition of matter that is useful for the treatment of killing microorganisms and human skin diseases, comprising the steps of:
    (a) preparing a sulfuric acid of 98 percent purity in a first container;
    (b) heating distilled water in a ratio of twice the volume of said sulfuric acid in a separate container to at least 140° F.;
    (c) mixing ammonium sulfate in said heated water in a ratio of 2.77 lbs. per gallon of water;
    (d) simultaneously combining the mixture of sulfuric acid, heated distilled water, and ammonium sulfate (mixture III) into a separate pressurized vessel by injection;
    (e) heating the pressurized mixture to at least 800° F. for at least 3 hours; and
    (f) cooling said mixture and adding a stabilizer in said cooled mixture, wherein said stabilizer comprises 10 weight percent of the total weight of mixture (III) whereby a composition of matter results that is useful for the treatment of killing deleterious microorganisms.

\* \* \* \* \*